(12) United States Patent
Matalon et al.

(10) Patent No.: US 9,587,759 B2
(45) Date of Patent: Mar. 7, 2017

(54) QUICK RELEASE VALVE COMPRESSOR

(71) Applicant: ITT MANUFACTURING ENTERPRISES LLC., Wilmington, DE (US)

(72) Inventors: Louis E. Matalon, Lancaster, PA (US); Michael D. Yoder, Quarryville, PA (US)

(73) Assignee: ITT MANUFACTURING ENTERPRISES LLC, Wilmington, DE (US)

( * ) Notice: Subject to any disclaimer, the term of this patent is extended or adjusted under 35 U.S.C. 154(b) by 418 days.

(21) Appl. No.: 14/032,822

(22) Filed: Sep. 20, 2013

(65) Prior Publication Data

US 2015/0083953 A1   Mar. 26, 2015

(51) Int. Cl.
| F16K 31/44 | (2006.01) |
| A61F 13/15 | (2006.01) |
| A61F 13/49 | (2006.01) |
| F16K 7/12 | (2006.01) |
| F16K 7/16 | (2006.01) |

(52) U.S. Cl.
CPC ........ *F16K 31/44* (2013.01); *A61F 13/15699* (2013.01); *A61F 13/15707* (2013.01); *A61F 13/4902* (2013.01); *F16K 7/12* (2013.01); *F16K 7/16* (2013.01)

(58) Field of Classification Search
CPC ... F16K 31/44; F16K 7/12; F16K 7/16; A61F 13/4902; A61F 13/15707; A61F 13/15699
USPC .............. 251/291, 366–367, 331, 335.2, 213
See application file for complete search history.

(56) References Cited

U.S. PATENT DOCUMENTS

| 2,620,134 A | 12/1952 | Obermaier |
| 2,647,692 A | 8/1953 | Keller et al. |
| 2,713,556 A | 7/1955 | Williams |

(Continued)

FOREIGN PATENT DOCUMENTS

| CA | 1039261 | 9/1978 |
| EP | 0897076 | 2/1999 |

(Continued)

OTHER PUBLICATIONS

The Pennsylvania State University, The Graduate School College of Engineering, "Modular Compressor Assembly for Diaphragm Valves" A Master of Engineering Paper by Louis E. Matalon, © 2009 Louis E. Matalon Submitted in Partial Fulfillment of the Requirements for the Degree of Master of Engineering in Engineering Science. May 2009, 36 pages.

(Continued)

*Primary Examiner* — Marina Tietjen
(74) *Attorney, Agent, or Firm* — Ware, Fressola, Maguire & Barber LLP (57) ABSTRACT

Apparatus is provided featuring a spindle having extending spindle portions configured with spindle glands; a compressor having extending compressor portions configured with compressor glands, and a snap ring configured to engage the spindle glands and the compressor glands in order to attach the spindle and compressor together, so that the compressor may be quickly released from the spindle by releasing an engagement between the snap ring, the spindle glands and/or the compressor glands.

18 Claims, 11 Drawing Sheets

Attachment of Compressor to Actuator Spindle

(56) References Cited

U.S. PATENT DOCUMENTS

| | | | |
|---|---|---|---|
| 2,716,394 | A | 8/1955 | Ray |
| 2,853,270 | A | 9/1958 | Boteler |
| 3,006,376 | A | 10/1961 | Schulze et al. |
| 3,021,859 | A | 2/1962 | Liantonio et al. |
| 3,038,488 | A | 6/1962 | Welch et al. |
| 3,079,950 | A | 3/1963 | Rimsha |
| 3,134,571 | A | 5/1964 | Boteler |
| 3,298,660 | A * | 1/1967 | Price ............... F16K 7/123 251/331 |
| 3,310,279 | A | 3/1967 | Boteler |
| 3,310,282 | A | 3/1967 | Boteler |
| 3,349,795 | A | 10/1967 | Matsutani |
| 3,700,206 | A | 10/1972 | Jones |
| 3,945,302 | A | 3/1976 | Downs |
| 3,958,603 | A | 5/1976 | Bannon et al. |
| 3,972,341 | A | 8/1976 | Wheless |
| 4,014,514 | A | 3/1977 | Priese et al. |
| 4,299,248 | A | 11/1981 | Becker et al. |
| 4,339,111 | A | 7/1982 | Welch |
| 4,354,666 | A | 10/1982 | McHale |
| 4,366,834 | A | 1/1983 | Hanson et al. |
| 4,400,131 | A | 8/1983 | Blake |
| 4,467,999 | A | 8/1984 | Ritter |
| 4,505,451 | A | 3/1985 | Jonas |
| 4,596,268 | A | 6/1986 | Jonas |
| 4,597,559 | A | 7/1986 | Kirk |
| 4,634,048 | A | 1/1987 | Hasse |
| 4,637,548 | A | 1/1987 | Ray et al. |
| 4,779,641 | A | 10/1988 | Charm et al. |
| 4,917,357 | A | 4/1990 | Danko |
| 4,979,527 | A | 12/1990 | Mueller et al. |
| 5,055,007 | A | 10/1991 | Geddings |
| 5,112,027 | A | 5/1992 | Hanyu et al. |
| 5,238,024 | A | 8/1993 | Taylor |
| 5,253,671 | A | 10/1993 | Kolenc |
| 5,277,401 | A | 1/1994 | Butler et al. |
| 5,377,956 | A | 1/1995 | Muller |
| 5,779,217 | A | 7/1998 | Lucas et al. |
| 5,823,509 | A | 10/1998 | Daniels |
| 5,871,156 | A | 2/1999 | Lawson |
| 5,899,386 | A | 5/1999 | Miyasato et al. |
| 5,996,608 | A | 12/1999 | Hunter et al. |
| 6,007,045 | A | 12/1999 | Heininger et al. |
| 6,047,953 | A | 4/2000 | Jacob, Jr. |
| 6,098,228 | A | 8/2000 | Chang |
| 6,142,442 | A | 11/2000 | Carroll |
| 6,227,455 | B1 | 5/2001 | Scott et al. |
| 6,241,213 | B1 | 6/2001 | Butler |
| 6,463,955 | B2 | 10/2002 | Hasak et al. |
| 6,491,235 | B1 | 12/2002 | Scott et al. |
| 6,789,781 | B2 | 9/2004 | Johnson et al. |
| 6,820,855 | B1 * | 11/2004 | Heller ............... F16K 7/12 137/485 |
| 6,851,449 | B2 | 2/2005 | Kleibrink |
| 6,854,664 | B2 | 2/2005 | Smith |
| 6,994,320 | B2 | 2/2006 | Johnson et al. |
| 7,021,330 | B2 | 4/2006 | Maula et al. |
| 7,059,584 | B2 | 6/2006 | Balasubramanian |
| 7,243,903 | B2 | 7/2007 | Wincek |
| 7,255,324 | B2 | 8/2007 | Schlude |
| 7,303,147 | B1 | 12/2007 | Danner et al. |
| 7,364,132 | B2 | 4/2008 | Browne et al. |
| 7,458,560 | B2 | 12/2008 | Muller |
| 7,694,934 | B2 | 4/2010 | Irwin |
| 8,430,376 | B1 | 4/2013 | Danner et al. |
| 2001/0037830 | A1 | 11/2001 | Sakurai |
| 2003/0042459 | A1 | 3/2003 | Gregoire |
| 2006/0065868 | A1 | 3/2006 | Strong |
| 2008/0202597 | A1 | 8/2008 | Chung |
| 2009/0020723 | A1 | 1/2009 | Masamura et al. |
| 2009/0095935 | A1 | 4/2009 | Wlodarczyk |
| 2012/0055555 | A1 | 3/2012 | Saint-Paul et al. |
| 2013/0008542 | A1 | 1/2013 | Irwin et al. |

FOREIGN PATENT DOCUMENTS

| | | |
|---|---|---|
| EP | 1154182 | 11/2001 |
| EP | 1417430 | 5/2004 |
| GB | 676019 | 7/1952 |
| GB | 720346 | 12/1954 |
| GB | 905322 | 9/1962 |
| GB | 939702 | 10/1963 |
| GB | 1534878 | 12/1978 |
| GB | 2004975 | 4/1979 |
| GB | 2097896 | 11/1982 |
| JP | 58-068570 | 4/1983 |
| JP | 2009208020 | 9/2009 |

OTHER PUBLICATIONS

EP0897076 English Language Abstract (1 page).
2009208020JP—15 pages English Language Translation.
58-068570JP—1 page English Language Abstract.
1417430EP—2 pages English Language Abstract.

\* cited by examiner

FIG. 1c:
Changing of the compressor and threaded tube-nut requires actuator disassembly for access to shear pin connection.

FIG. 1b:
Elastomer Diaphragm Configuration requiring Threaded Compressor

FIG. 1a:
PTFE Diaphragm Configuration requiring Threaded Tube Nut

FIG. 1: Typical Use of Shear Pin for Compressor to Spindle Connection (PRIOR ART) Using Fixed Compressor Connection

FIG. 2: Design for Easy Change Out of Compressor, Tube Nut & Diaphragm Material Type, Using Known ADV 2.0 Free Compressor Connection
(PRIOR ART)

Note: Compressor and Tube-Nut are free when diaphragm is removed.

FIG. 3a: GEMU

FIG. 3b: SED

FIG. 3c: BSS

FIG. 3: Showing Three Known Methods for Compressor Attachment using Diaphragm, where the Compressor is Free to Fall from the Actuator Assembly when the Diaphragm is Removed (PRIOR ART)

FIG. 4a: Attachment of Compressor to Actuator Spindle

FIG. 4: Invention – Quick Release Compressor for Diaphragm Valves

FIG. 4f: ATTACHMENT AND REMOVAL COMPRESSOR TO ACTUATOR SPINDLE

FIG. 5b

FIG. 5a: Geometry Designed for Machined Spindle, Showing Similar Snap on and Snap Off Performance as the Previously Described Quick Release Compressor, Using a Cast Spindle Design FIG. 6a      FIG. 6b      FIG. 6c FIG. 6d      FIG. 6e FIG. 7: Force to Install Quick Release Valve Compressor

QUICK RELEASE VALVE COMPRESSOR

BACKGROUND OF THE INVENTION

1. Field of the Invention

The present invention relates to a technique for replacing a compressor in a valve; and more particularly relates to a technique for replacing a compressor in a diaphragm valve, including one having a weir.

2. Brief Description of Related Art

In traditional designs, compressor replacement typically requires actuator dismantling. In recent designs, the compressor is held in place by the diaphragm. During regular maintenance of diaphragm replacement, the compressor can fall off the assembly.

Known diaphragms by the assignee of the instant patent application use two thread sizes, distinguishing diaphragm material. These diaphragms and the attachment methods associated with the same are known in the industry, and may also be referred to as the "ITT Advantage attachment method." Changing between these materials requires reconstruction of the actuator in order to replace the mating compressor and thread components. A known assembly technique by the assignee of the present application allows these components in the known diaphragm to be easily changed on the customer process line. These diaphragms and the attachment methods associated with the same are known in the industry, and may also be referred to as the "ITT Advantage, ADV, 2.0 attachment method." However, one disadvantage of the known technique is that the interchangeable components are loose during regular diaphragm replacement. Modern competitor systems have a similar situation and a similar problem.

Figure 1A:
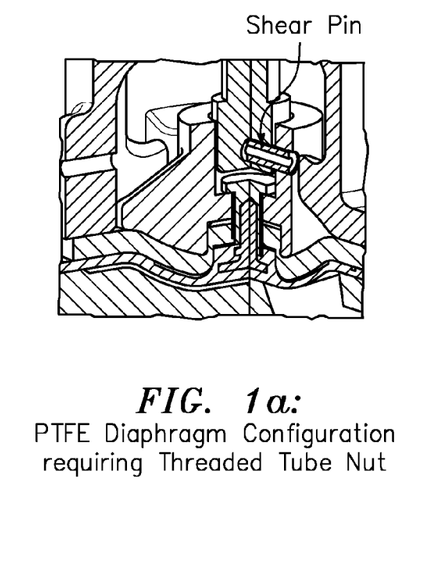
FIG. 1a shows a ¾ cross-section view of part of a valve having a PTFE diaphragm configuration requiring a threaded tube nut; where
Figure 1B:
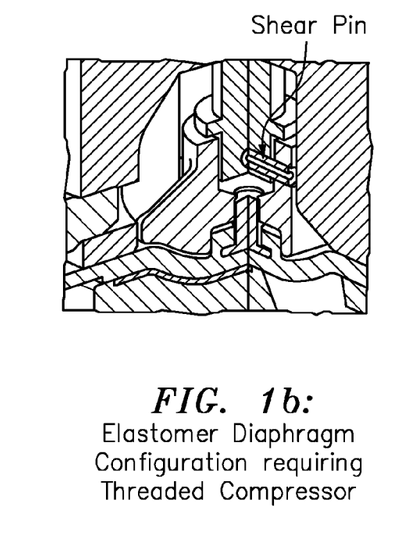
FIG. 1b shows a ¾ cross-section view of part of a valve having an elastomer diaphragm configuration requiring a threaded compressor.
Figure 1C:
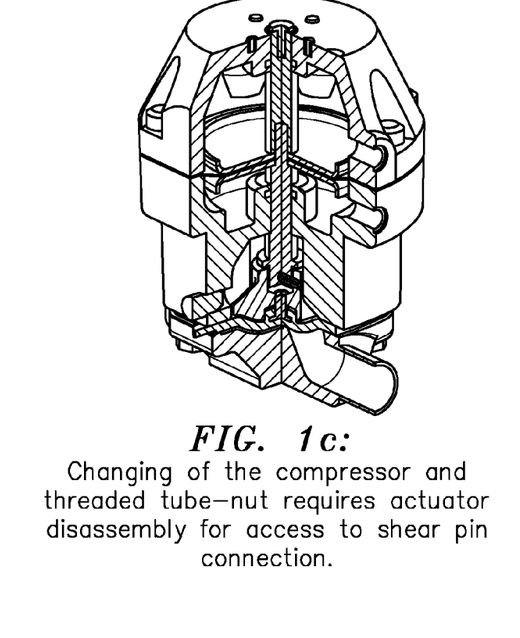
FIG. 1c shows a ¾ cross-section view of part of a valve, in which the changing of the compressor and threaded tube-nut requires actuator disassembly for access to a shear pin connection.
Figure 2:
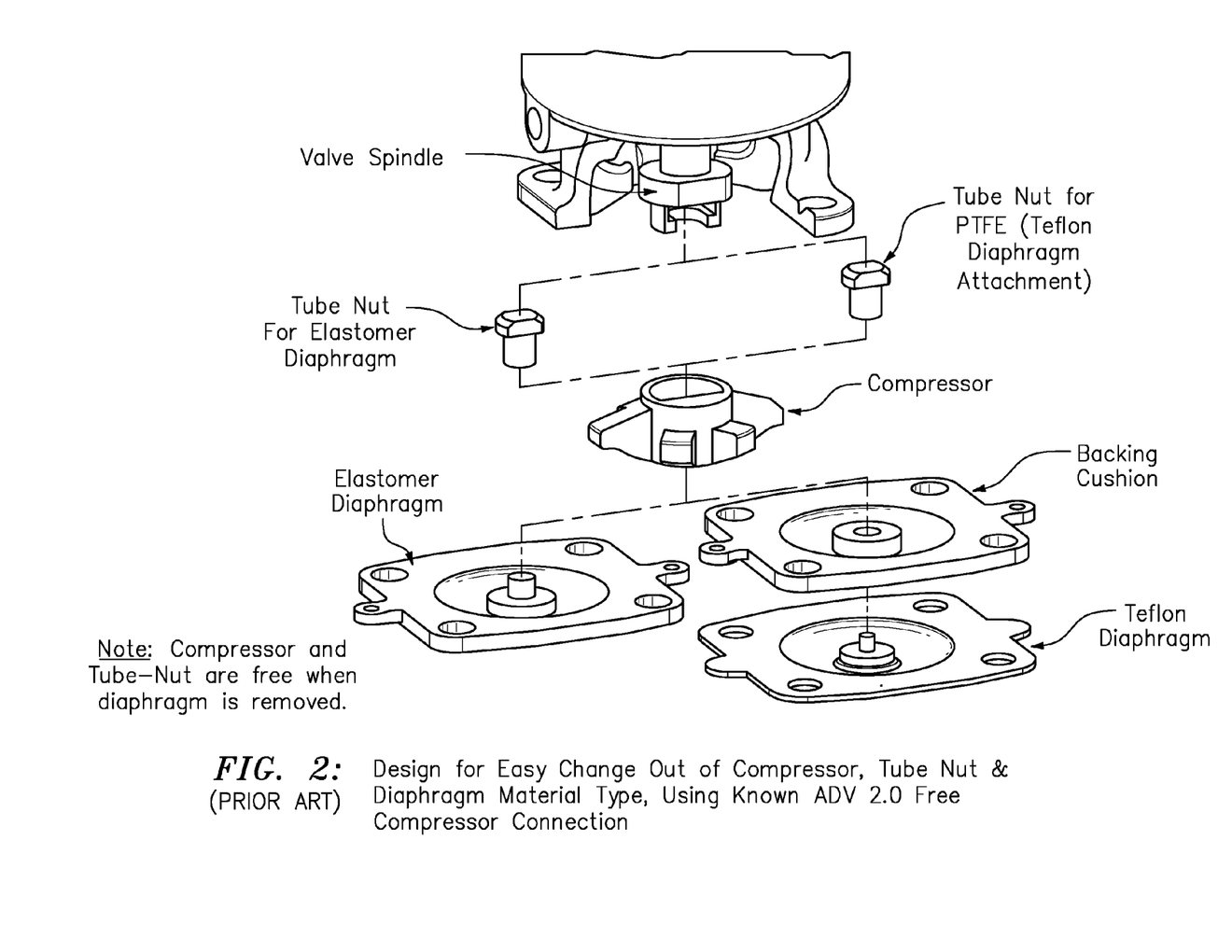
FIG. 2 shows an exploded view of a design for easy change out of a compressor, tube nut and diaphragm material type, using the aforementioned known ADV 2.0 free compressor connection.

FIGS. 1-3 show examples of prior art designs.

For example, FIG. 1 shows typical uses of a shear pin for compressor-to-spindle connections using fixed compressor connections that are known in the art. FIG. 1a shows part of a valve having a PTFE diaphragm configuration requiring a threaded tube nut. FIG. 1b shows part of a valve having an elastomer diaphragm configuration requiring a threaded compressor. FIG. 1c shows part of a valve, in which the changing of the compressor and threaded tube-nut requires actuator disassembly for access to a shear pin connection.

Moreover, FIG. 2 shows a design for easy change out of a compressor, tube nut and diaphragm material type, using the aforementioned ADV 2.0 free compressor connection.

Figures 3A, 3B, 3C:
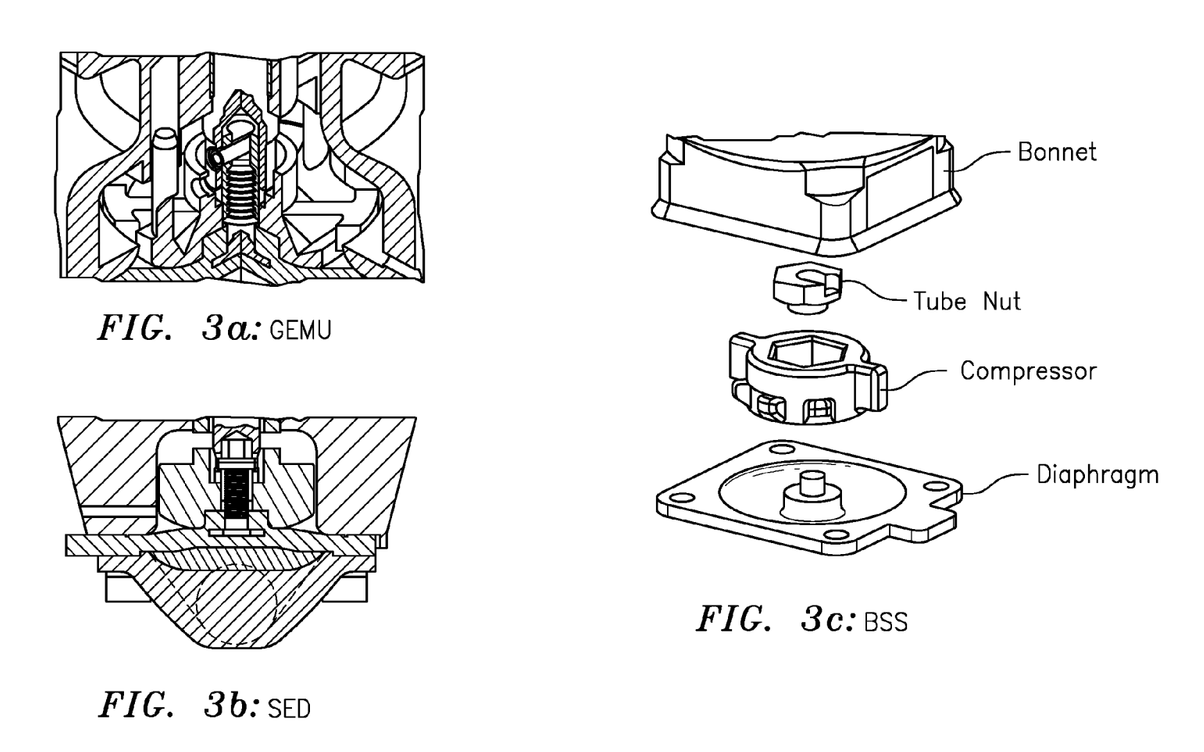
FIG. 3a shows a ¾ cross-section view of part of a known GEMU valve, where
FIG. 3b shows a partial side view of part of a known SED valve, and where
FIG. 3c shows an exploded view of part of a known BBS valve.

Moreover still, FIG. 3 shows three known methods for compressor attachment, where the compressor is free to fall from the actuator assembly when the diaphragm is removed. For example, FIG. 3a shows part of a known GEMU valve. FIG. 3b shows part of a known SED valve. FIG. 3c shows part of a known BBS valve.

There is a need in the industry for a better way to avoid having all these loose components during regular diaphragm replacement.

SUMMARY OF THE INVENTION

Brief Summary

In summary, the present invention builds upon many advantages of the aforementioned known assembly technique by the assignee of the present application, while eliminating the drawback of having loose parts during typical maintenance diaphragm changes. According to the present invention, during diaphragm changes a compressor may be held in place on the actuator assembly with a snap ring, e.g., using a commercial snap ring. The compressor can be pried off with a moderate force when the compressor and/or contained parts are changed out. In addition to use in valves, this unique use of the snap ring may be applicable to many other products in many other industries.

This compressor retention method according to the present invention may be used in most diaphragm valves. In a broader stroke, use of a snap ring to attach two parts with only the inner gland wall by way of sharing the peripheral space of engagement forms part of another unique concept implemented herein. This may also be applied to sharing the outer gland wall, as well as attaching a multitude of components with the inner gland wall, and/or the outer gland wall, etc.

When the present invention is implemented, the compressor and threaded component that attaches to the diaphragm can be easily replaced, yet do not fall loose during normal diaphragm maintenance. Furthermore, security of the compressor and threaded component during operation is ensured by the diaphragm connection. This capability has been strongly requested by people in the industry, e.g. including customers of the assignee of the instant patent application.

Summary of Particular Embodiments

According to some embodiments, the present invention features apparatus, that may include, or take the form of, a quick release compressor combination, e.g., that may be used in a diaphragm valve, such as a weir-type diaphragm valve. The quick release compressor combination may include a spindle, a compressor and a snap ring. The spindle may include extending spindle portions configured with spindle glands. The compressor may include extending compressor portions configured with compressor glands. The snap ring may be configured to engage the spindle glands and the compressor glands in order to attach the spindle and the compressor together, so that the compressor may be quickly released from the spindle by releasing an engagement between the snap ring, the spindle glands and/or the compressor glands.

The present invention may also include one or more of the following features:

The design is disclosed herein to have the spindle detach from the compressor/snap-ring sub-assembly, however, could be made to have the compressor detach from the spindle/snap-ring sub-assembly.

The spindle glands may be configured for facing outwardly away from the center of the spindle; the compressor glands may also be configured for facing outwardly away from the center of the compressor; and the snap ring may be configured to engage the spindle glands and the compressor glands so as to form a shared exterior gland.

Alternatively, the spindle glands may be configured for facing inwardly towards the center of the spindle; the compressor glands may be configured for facing inwardly towards the center of the compressor; and the snap ring may be configured to engage the spindle glands and the compressor glands so as to form a shared interior gland. In other words, the scope of the invention is not intended to be limited to the direction in which the spindle or compressor glands are facing.

The extending spindle portions may be configured on diametrically opposite sides of an end portion of the spindle; and the extending compressor portions may be configured on diametrically opposite sides of a center portion of the compressor. The extending spindle portions and the extending compressor portions may also be configured to mate and interlock when the snap ring engages the spindle glands and the compressor glands in order to attach the spindle and compressor together.

The extending spindle portions, or the extending compressor portions, or both the extending spindle portions and the extending compressor portions, may be configured as partial cylindrical portions having partial cylindrical glands.

The spindle has a longitudinal axis, and the extending spindle portions may be configured to extend substantially in parallel with the longitudinal axis of the spindle. Moreover, the compressor has a central axis coaxial with the longitudinal axis of the spindle, and the extending compressor portions may be configured to extend substantially in parallel with the central axis of the compressor. The snap ring may be configured to engage the spindle glands and the compressor glands on a plane substantially perpendicular to the longitudinal axis of the spindle.

The spindle glands and compressor glands may be configured as, or formed part of, a protruding rim, edge, rib, or collar on the extending spindle portions or the extending compressor portions.

The extending spindle portions may include inwardly extending flanges configured to receive and engage outwardly extending flanges of, e.g., a tube nut that forms part of a diaphragm attachment; and the snap ring may be configured to engage the extending spindle portions in order to resist outward movement of the inwardly extending flanges and maintain a coupling, e.g., with the tube nut. The coupling between the inwardly extending flanges of the extending spindle portions and the outwardly extending flanges of the tube nut primarily holds the compressor in place during operation.

The snap ring may include one side having a flat circumferential surface configured to engage the spindle glands; and the snap ring may also include an opposite side having a corresponding flat circumferential surface configured to engage the compressor glands.

The snap ring may include an inner circumferential rim or surface configured to engage respective cylindrical wall portions, channels or grooves of the spindle glands and the compressor glands, so as to hold the snap ring in place.

The snap ring, the spindle glands and the compressor glands may be configured to allow the compressor rotational freedom, e.g., on a single axis.

The spindle may be made by a cast spindle design, or by either turning and milling, based at least partly on the fact that the spindle is configured without difficult interior cuts.

The present invention may be implemented, e.g., in applicable products that may include diaphragm valves, including low cost actuator for bio pure diaphragm valves.

The present invention may also have other applications, e.g., vis-a-vis compressor attachment to linear actuator valves.

BRIEF DESCRIPTION OF THE DRAWING

The drawing includes the following Figures, not necessarily drawn to scale:

FIG. 1 includes FIGS. 1a to 1c and shows typical uses of a shear pin for compressor-to-spindle connections using a fixed compressor connection that are known in the art, where

FIG. 3 includes FIGS. 3a to 3c and shows three known methods for compressor attachment, where the compressor is free to fall from the actuator assembly when the diaphragm is removed, where

FIG. 6 includes FIGS. 6a to 6e and shows the present invention in the form of a quick release compressor combination having a snap ring on a shared interior gland, where

In the following description of the exemplary embodiment, reference is made to the accompanying Figures in the drawing, which form a part hereof, and in which are shown by way of illustration of an embodiment in which the invention may be practiced. It is to be understood that other embodiments may be utilized, as structural and operational changes may be made without departing from the scope of the present invention.

Further, in an effort to reduce clutter in the drawing, each element or component set forth in the detailed description below is not necessarily indicated with its respective reference label and lead line in every Figure of the drawing.

DETAILED DESCRIPTION OF THE INVENTION

The Basic Invention

According to some embodiments, the present invention may take the form of apparatus generally indicated as 10 (see FIG. 4a), e.g., that includes, or takes the form of, a quick release compressor combination, e.g., that may be used in a diaphragm valve, such as a weir-type diaphragm valve. The apparatus 10 features at least in part a combination of a spindle 12, a compressor 14 and a snap ring 16, consistent with that shown in FIGS. 4 to 6.

By way of example, the spindle 12 may include extending spindle portions 12a', 12a" configured with spindle glands 12b', 12b". The compressor 14 may include extending compressor portions 14a', 14a" configured with compressor glands 14b', 14b". In operation, the snap ring 16 may be configured to engage the spindle glands 12b', 12b" and the compressor glands 14b', 14b" in order to attach the spindle 12 and the compressor 14 together, so that the compressor 14 may be quickly released from the spindle 12 by releasing an engagement between the snap ring 16, the spindle glands 12b', 12b" and the compressor glands 14b', 14b".

FIG. 4

Detailed Discussion

Figures 4, 4A:
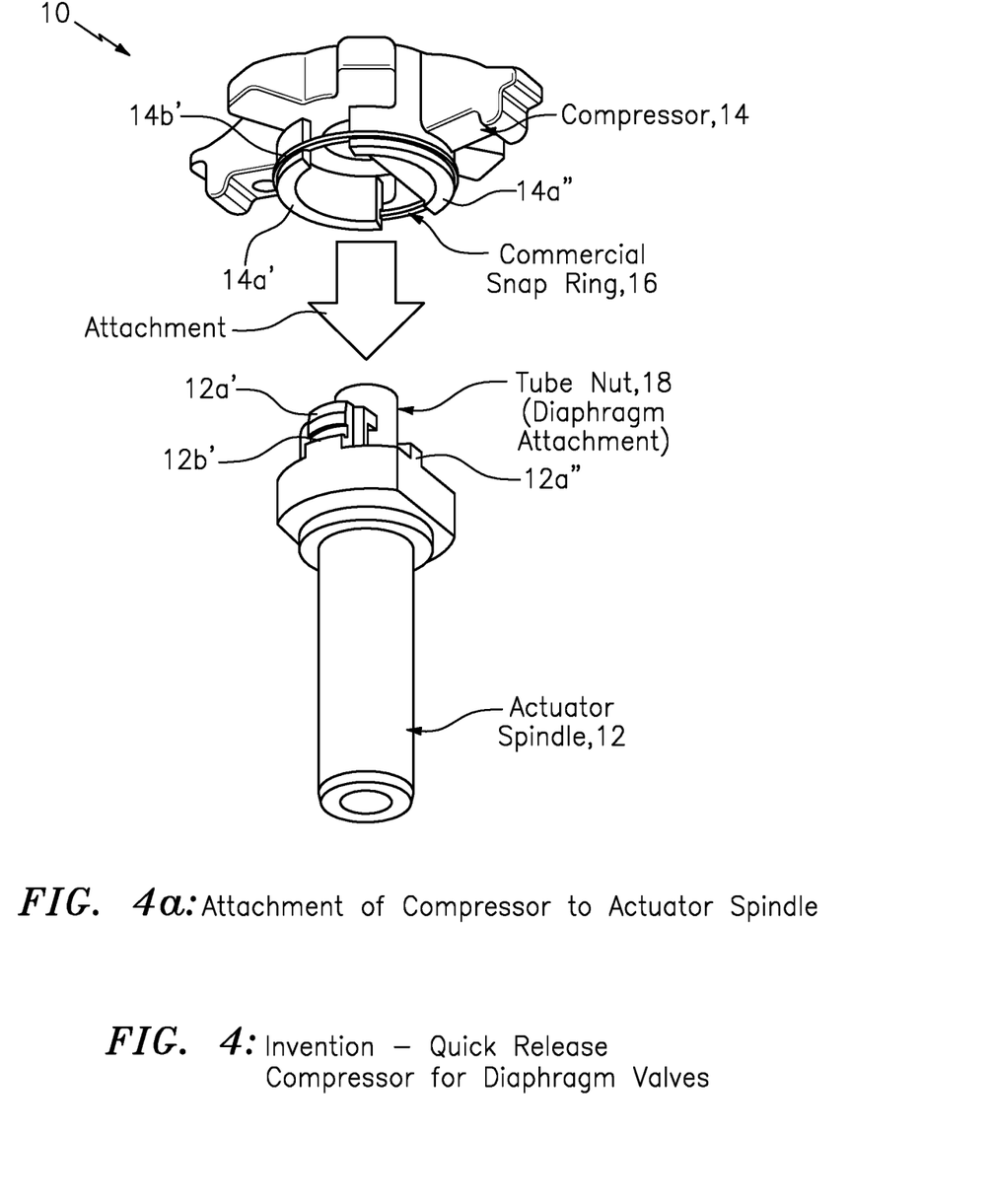
FIG. 4 includes FIGS. 4a to 4f and shows the present invention in the form of a quick release compressor combination for use in diaphragm valves, according to some embodiments of the present invention, where
FIG. 4a shows an exploded view of apparatus for forming an attachment between a spindle, a compressor and a snap ring, according to some embodiment of the present invention; where
Figures 4B, 4C:
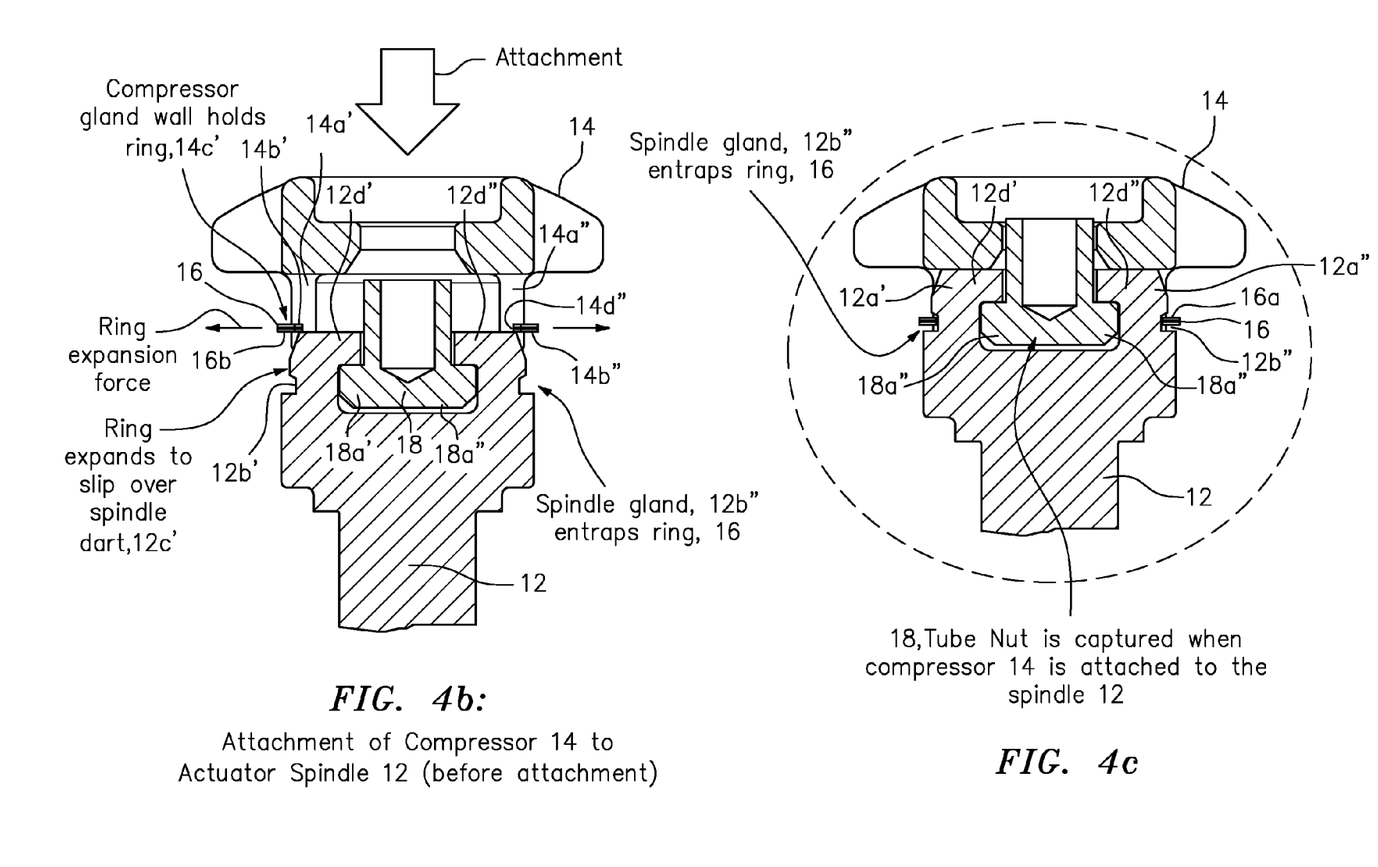
FIG. 4b shows a cross-sectional view of part of the apparatus shown in FIG. 4a for forming the attachment between the spindle, the compressor and the snap ring, according to some embodiment of the present invention; where
FIG. 4c shows a cross-sectional view of the apparatus shown in FIG. 4b after the attachment between the spindle, the compressor and the snap ring, according to some embodiment of the present invention; where FIG. 4d(1) shows a ¾ cross-sectional view of the apparatus shown in FIG. 4c, according to some embodiment of the present invention; where FIG. 4d(2) shows an isometric view of the apparatus shown in FIG. 4c, according to some embodiment of the present invention; where FIG. 4e(1) shows a side view of the apparatus shown in FIG. 4d(2), according to some embodiment of the present invention; where FIG. 4e(2) shows a ¾ cross-sectional view of the apparatus shown in FIG. 4e(1) arranged in a bonnet, according to some embodiment of the present invention; where
Figure 4D:
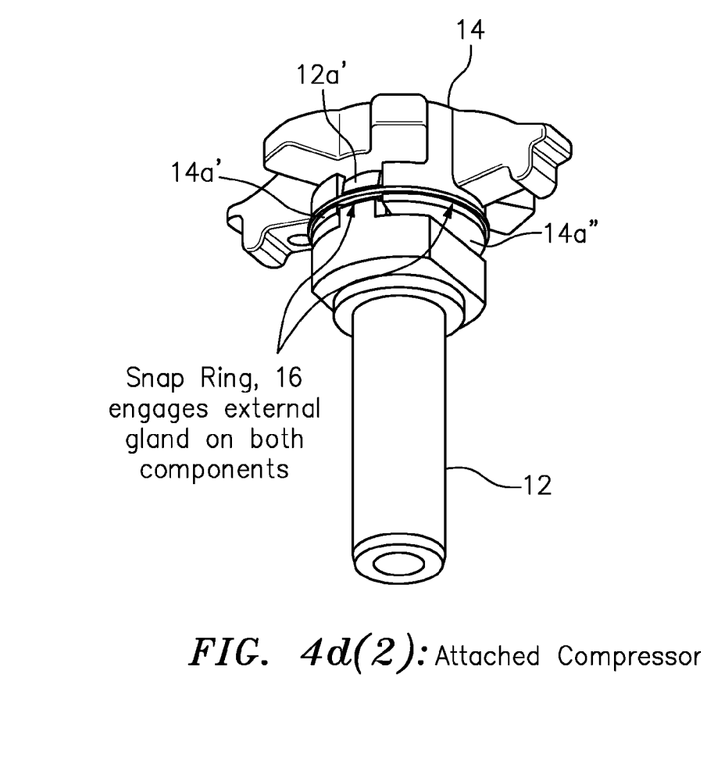
Figure 4E:
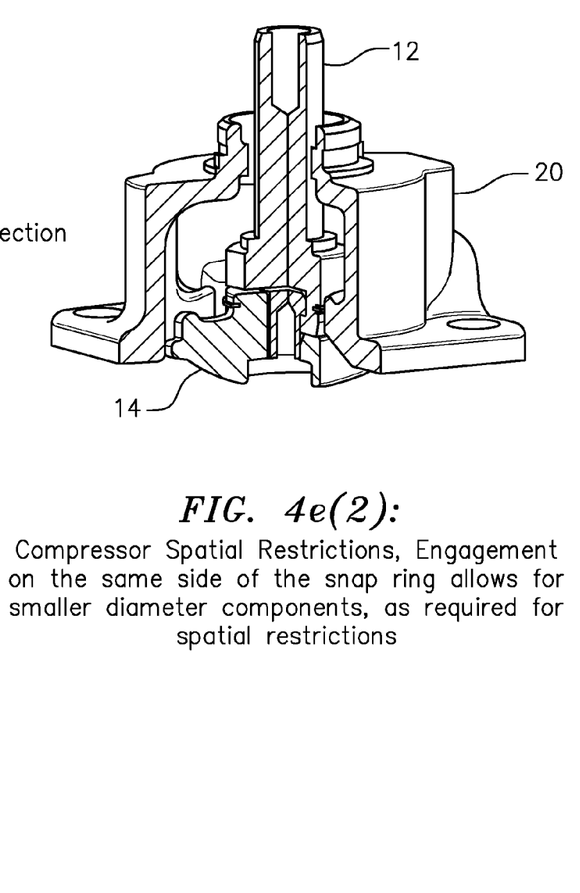
Figure 4F:
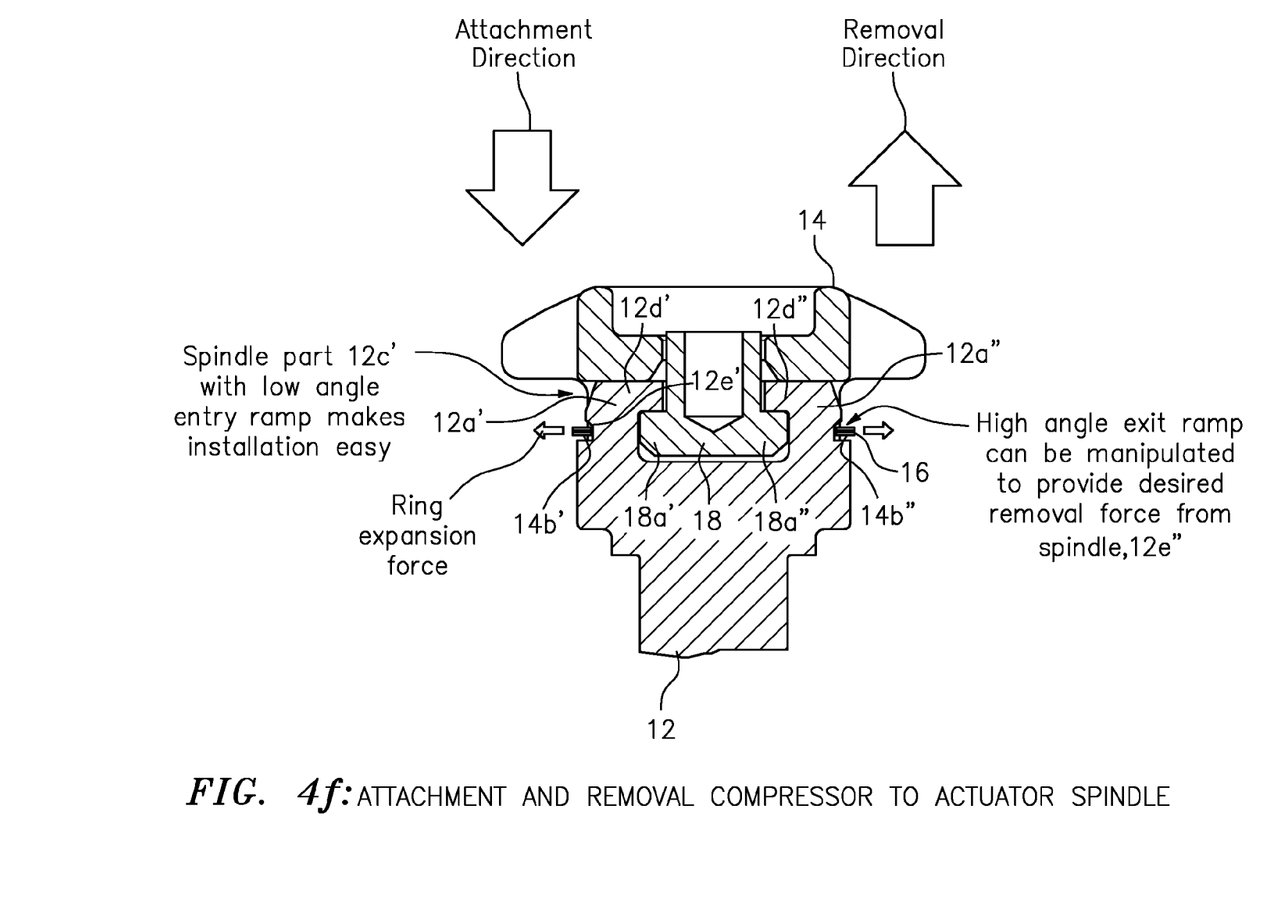
FIG. 4f shows an enlarged view of the apparatus shown in FIG. 4c, according to some embodiment of the present invention.

In particular, FIGS. 4a and 4b shows the spindle 12, the compressor 14 and the snap ring 16 before their attachment. FIG. 4a also shows a tube nut 18, e.g., that forms part of a diaphragm attachment. FIG. 4b shows a beveled portion 12c configured on the extending spindle portions 12a, 12a" of the spindle 12, and how the snap ring 16 may expand to slip over the beveled portion 12c (also referred to herein as a spindle dart). FIGS. 4c, 4d(1), 4d(2), 4e(1), 4e(2) and 4f all show the quick release compressor combination after the attachment between the spindle 12, the compressor 14 and the snap ring 16. In FIGS. 4b and 4c, the compressor 14 has gland walls, one of which is indicated by reference label 14c', that each may be configured with, or configured as, a respective compressor gland wall channel or groove, one of which is indicated by reference label 14d" to hold the slip ring 16 therein. FIGS. 4b and 4c show the spindle glands 12b', 12b", and how the spindle glands 12a', 12a" entrap the snap ring 16 (see FIG. 4c). FIG. 4c also shows how the tube nut 18 is captured within the spindle portions 12a', 12a" when the compressor 14 is attached to the spindle 12. FIGS. 4d(1) and 4d(2) show how the snap ring 16 engages the spindle glands 12b', 12b" and the compressor glands 14b', 14b" on both components. FIG. 4e(1) shows how the snap ring 16, the spindle glands the spindle glands 12b', 12b" and the compressor glands 14b', 14b" may be configured to allow the compressor 14 limited rotational freedom on a single axis, so as to allow the compressor 14 of the quick release compressor combination to move in the rotational directions as shown. FIG. 4e(2) shows the attached quick release compressor combination shown in FIGS. 4c, 4d(1), 4d(2), 4e(1), 4e(2) and 4f arranged in relation to a bonnet 20 that may form part of a diaphragm valve. FIG. 4e(2) illustrates how engagement on the same side (e.g., the inside rim portion) of the snap ring 16 can allow for components having a smaller diameter, as required in some applications having special compressor spatial restrictions. FIG. 4f shows how beveled portions, one of which is labeled 12c' (see also FIG. 4b), may be configured with, or take the form of, a low angle entry ramp that makes for an easy installation of the snap ring 16 in relation to the spindle glands 12b', 12b" and the compressor glands 14b', 14b". FIG. 4f also shows high angle exit ramps, one of which is labeled 12e"', configured on the extending spindle portions 12a', 12a" of the spindle 12 that can be manipulated or configured to provide for a desired removal force of the snap ring 16 from the attached combination of the spindle 12 and compressor 14. In FIG. 4f, an attachment direction and a removal direction is indicated by the respectively labeled arrows.

By way of example, the spindle 12 in FIG. 4 may be configured or manufactured using a cast design process.

FIG. 5a, 5b

Detailed Discussion

Figure 5A:
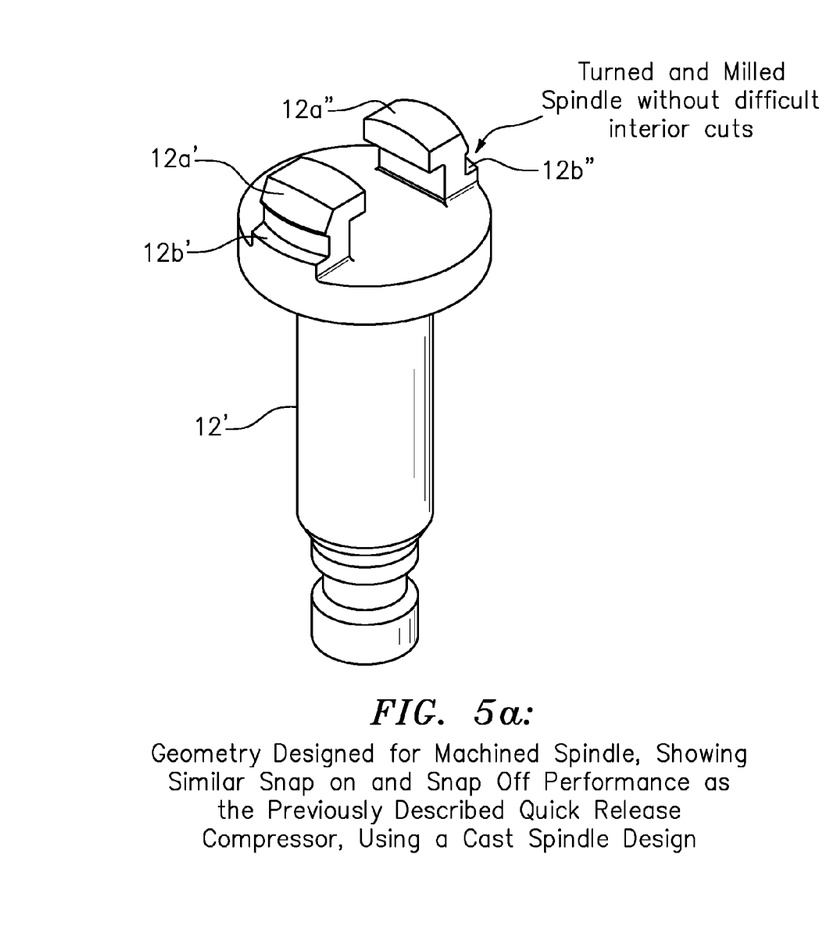
FIG. 5a shows an isometric view of a spindle that forms part of the apparatus, according to some embodiment of the present invention.

Alternatively, FIG. 5a shows a machine spindle 12' having a geometric design that is configured without difficult interior cuts so that the spindle 12 can be manufactured, e.g., by being turned and milled. The spindle 12' in FIG. 5a can be manufactured or configured with a similar snap on and snap off performance as the spindle 12 in FIG. 4 using the cast design.

FIGS. 4-5

The Shared Exterior Gland Embodiment

Figure 5B:
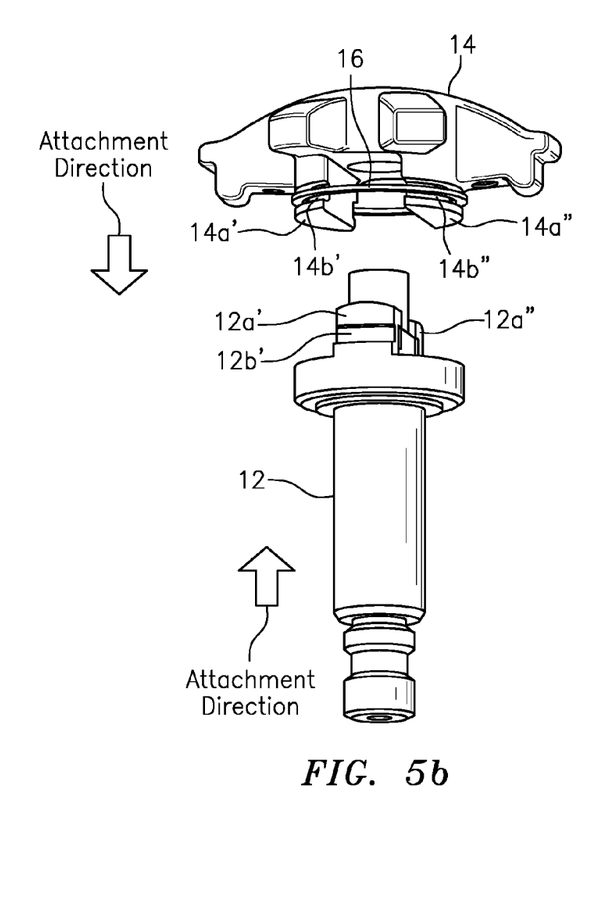
FIG. 5b shows an exploded view of the apparatus for forming an attachment between a spindle, a compressor and a snap ring, according to some embodiment of the present invention.

By way of example, and consistent with that shown in FIGS. 4-5, the quick release compressor combination may be configured with a shared exterior gland, and may include one or more of the following features particular to this embodiment:

The spindle glands 12b', 12b" may be configured to face outwardly away from the center of the spindle 12, as shown; the compressor glands 14b', 14b" may also be configured to face outwardly away from the center of the compressor 14, as shown; and the snap ring 16 may be configured to engage the spindle glands 12b', 12b" and the corresponding compressor glands 14b', 14b" so as to form the shared exterior gland.

The spindle glands 12b', 12b" and the compressor glands 14b', 14b" may be configured as, or formed part of, a protruding rim, edge, rib, collar, groove or channel on the extending spindle portions 12a', 12a" or the extending compressor portions 14a', 14a", as shown.

The extending spindle portions 12a', 12a" may include inwardly extending flanges 12d', 12d" configured to receive and engage outwardly extending flanges 18a', 18a" of the tube nut 18, e.g., that forms part of the diaphragm attachment; and the snap ring 16 may be configured to engage the extending spindle portions 12a', 12a" in order to resist outward movement of the inwardly extending flanges 12d', 12d" and maintain a coupling with the tube nut 18. The coupling between the inwardly extending flanges 12d', 12d" of the extending spindle portions 12a', 12a" and the outwardly extending flanges 18a', 18a" of the tube nut 18 primarily holds the compressor 14 in place during operation, e.g., of the diaphragm valve.

The snap ring 16 may include one side having a flat circumferential surface 16a configured to engage the spindle glands 12b', 12b"; and the snap ring 16 may also include an opposite side having a corresponding flat circumferential surface 16b configured to engage the compressor glands 14b', 14b". The snap ring 16 may include an inner circumferential rim or surface configured to engage respective cylindrical wall portions or channels formed therein of the spindle glands 12b', 12b" and the compressor glands 14b', 14b".

FIGS. 4-6

Some General Features of the Quick Release Compressor Combination

By way of example, and consistent with that shown in FIGS. 4-6, the quick release compressor combination in general may include one or more of the following features:

The extending spindle portions 12a', 12a" may be configured on diametrically opposite sides of an end portion of the spindle 12, as shown; and the extending compressor portions 14a', 14a" may be configured on diametrically opposite sides of a center portion of the compressor 14, as also shown. The extending spindle portions 12a', 12a" and the extending compressor portions 14a', 14a" may also be configured to mate and interlock when the snap ring 16 engages the spindle glands 12b', 12b" and the compressor glands 14b', 14b" in order to attach the spindle 12 and compressor 14 together, as shown.

Either the extending spindle portions 12a', 12a", or the extending compressor portions 14a', 14a", or both, may be configured as partial cylindrical portions having partial cylindrical glands, as shown.

The spindle 12 has a longitudinal axis, and the extending spindle portions 12a', 12a" may be configured to extend substantially in parallel with the longitudinal axis of the spindle 12, as shown. Moreover, the compressor 14 has a central axis coaxial with the longitudinal axis of the spindle 12, as shown, and the extending compressor portions 14a', 14a" may be configured to extend substantially in parallel with the central axis of the compressor 14, as also shown. The snap ring 16 may be configured to engage the spindle glands 12b', 12b" and the compressor glands 14b', 14b" on a plane substantially perpendicular to the longitudinal axis of the spindle 12, as shown.

FIG. 6

The Shared Interior Gland Embodiment

FIG. 6 shows an alternative embodiment of the present invention in the form of a quick release compressor combination having a shared interior gland. In FIG. 6, by way of example, the top element is indicated to be part of the spindle 12, and the bottom element is indicated to be part of the compressor 14; however, it is understood that the top element could be indicated to be part of the compressor 14, and the bottom element could be indicated to be part of the spindle 12 within the scope and spirit of the present invention.

Figure 6A:
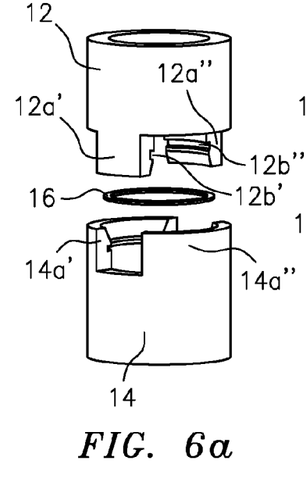
FIG. 6a shows an exploded view of apparatus having a spindle, a compressor and a snap ring, before attachment, according to some embodiment of the present invention; where
Figure 6B:
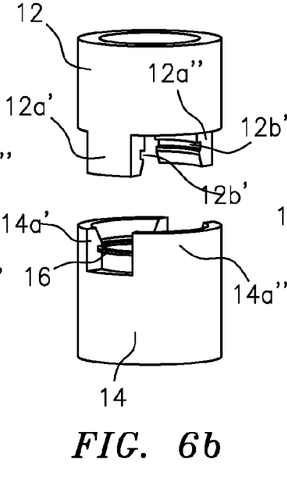
FIG. 6b shows an exploded view of the apparatus shown in FIG. 6a with the snap ring configured in the compressor, according to some embodiment of the present invention; where
Figure 6C:
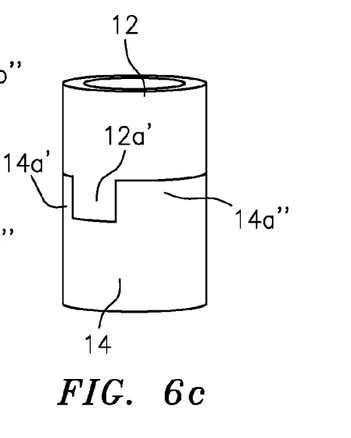
FIG. 6c shows a view of the apparatus shown in FIG. 6b with the compressor and spindle attached together, according to some embodiment of the present invention; where
Figure 6D:
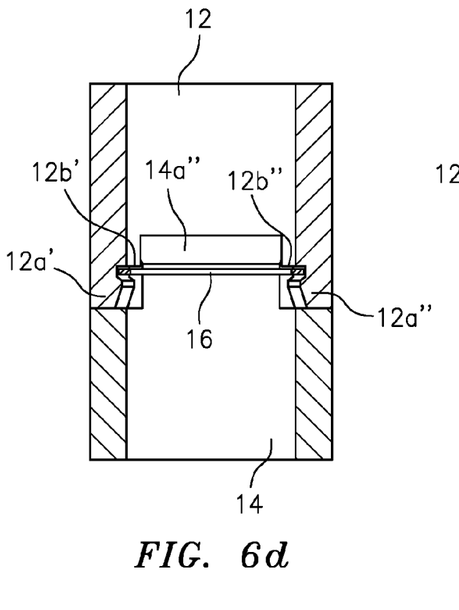
FIG. 6d shows a cross-sectional view of the apparatus shown in FIG. 6c with the compressor and spindle attached together by the snap ring, according to some embodiment of the present invention; and where

In FIG. 6, the spindle glands 12b', 12b" may be configured for facing inwardly towards the center of the spindle; the compressor glands 14b' (see FIG. 6e) may also be configured for facing inwardly towards the center of the compressor 14; and the snap ring 16 may be configured to engage the spindle glands 12b, 12b" and the compressor glands 14b' so as to form the shared interior gland, as best shown in FIG. 6d.

Figure 6E:
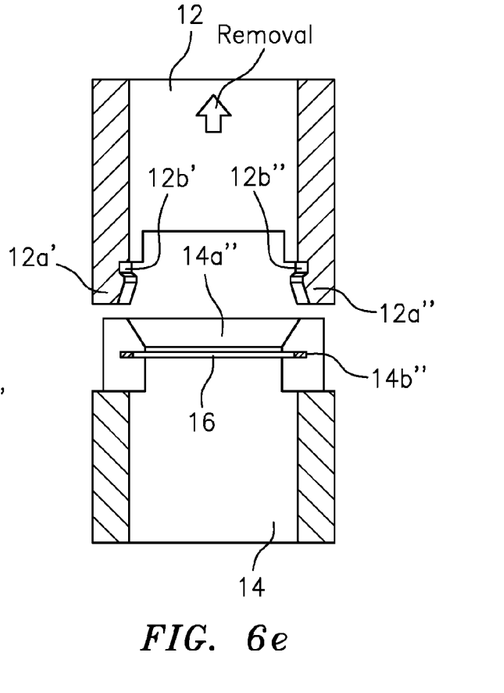
FIG. 6e shows an exploded cross-sectional view of the apparatus shown in FIG. 6d with the spindle removed from the compressor, according to some embodiment of the present invention.
Figure 7:
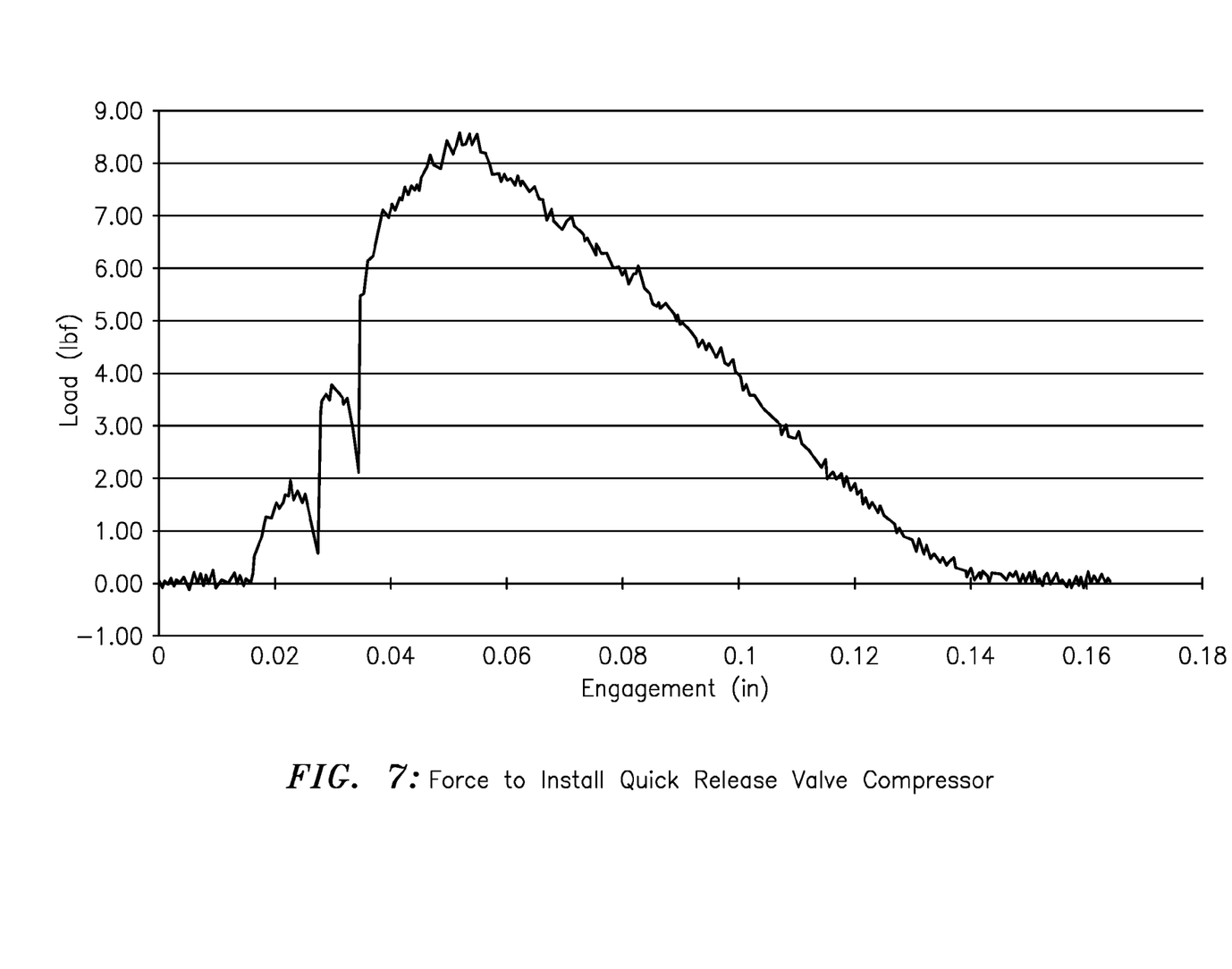
FIG. 7 shows a graph of load (lbf) versus engagement (inches) of the force to install or attach the quick release compressor combination according to some embodiment of the present invention.

In particular, FIG. 6a shows the combination of the spindle 12, the compressor 14 and the snap ring 16, before attachment. FIG. 6b shows the snap ring 16 configured in the compressor 14. FIG. 6c shows the spindle 12 and the compressor 14 attached together. FIG. 6d shows the spindle 12 and the compressor 14 attached together by the snap ring 16. FIG. 6e shows the spindle 12 removed from the compressor 14.

The Scope of the Invention

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

In particular, the scope of the invention is intended to include implementing the present invention in conjunction with the numerous embodiments set forth in the related applications set forth herein.

By way of example, the instant patent application sets forth two geometries or configurations for implementing the present invention. However, the scope of the invention is intended to include, and embodiments are envisioned, using other types or kinds of geometries either now known or later developed in the future within the spirit of the present invention, e.g., including other types or kinds of geometries for configuring the spindle, the compressor, or the snap ring for engaging and attaching the spindle and compressor together, so that the compressor may be quickly released from the spindle by releasing an engagement between the snap ring and portions of the spindle and the compressor.

What we claim is:
1. Apparatus comprising:
a spindle having extending spindle portions configured with spindle glands;
a compressor having extending compressor portions configured with compressor glands, and
a snap ring configured to engage the spindle glands and the compressor glands in order to attach the spindle and the compressor together, so that the compressor may be quickly released from the spindle by releasing an engagement between the snap ring, the spindle glands and/or the compressor glands; wherein
the extending spindle portions comprise inwardly extending flanges configured to receive and engage outwardly extending flanges of a tube nut that forms part of a diaphragm attachment; and the snap ring is configured to engage the extending spindle portions in order to resist outward movement of the inwardly extending flanges and maintain a coupling with the tube nut.

2. Apparatus according to claim 1, wherein
the spindle glands are configured far facing outwardly away from the center of the spindle;
the compressor glands are also configured for facing outwardly away from the center of the compressor; and
the snap ring is configured to engage the spindle glands and the compressor glands so as to form a shared exterior gland.

3. Apparatus according to claim 1, wherein
the spindle glands are configured for facing inwardly towards the center of the spindle;
the compressor glands are configured for facing inwardly towards the center of the spindle or the compressor; and
the snap ring is configured to engage the spindle glands and the compressor glands so as to form a shared interior gland.

4. Apparatus according to claim 1, wherein
the extending spindle portions are configured on diametrically opposite sides of an end portion of the spindle; and
the extending compressor portions are configured on diametrically opposite sides of a center portion of the compressor.

5. Apparatus according to claim 4, wherein
the extending spindle portions and the extending compressor portions are configured to mate and interlock when the snap ring engages the spindle glands and the compressor glands in order to attach the spindle and compressor together.

6. Apparatus according to claim 1, wherein the extending spindle portions, or the extending compressor portions, or both the extending spindle portions and the extending compressor portions, are configured as partial cylindrical portions having partial cylindrical glands.

7. Apparatus according to claim 1, wherein the spindle has a longitudinal axis, and the extending spindle portions are configured to extend substantially in parallel with the longitudinal axis of the spindle.

8. Apparatus according to claim 7, wherein the compressor has a central axis coaxial with the longitudinal axis of the spindle, and the extending compressor portions are configured to extend substantially in parallel with the central axis of the compressor.

9. Apparatus according to claim 8, wherein the snap ring is configured to engage the spindle glands and the compressor glands on a plane substantially perpendicular to the longitudinal axis of the spindle.

10. Apparatus according to claim 1, wherein the spindle glands and compressor glands are configured as, or formed part of, a protruding rim, edge, rib, or collar on the extending spindle portions or the extending compressor portions.

11. Apparatus according to claim 1, wherein the coupling between the inwardly extending flanges of the extending spindle portions and the outwardly extending flanges of the tube nut primarily holds the compressor in place during operation.

12. Apparatus according to claim 1, wherein
the snap ring comprises one side having a flat circumferential surface configured to engage the spindle glands; and
the snap ring comprises an opposite side having a corresponding flat circumferential surface configured to engage the compressor glands.

13. Apparatus according to claim 1, wherein
the snap ring comprises an inner circumferential rim or surface configured to engage respective cylindrical wall portions of the spindle glands and the compressor glands.

14. Apparatus according to claim 1, wherein the snap ring, the spindle glands and the compressor glands are configured to allow the compressor rotational freedom on a single axis.

15. Apparatus according to claim 1, wherein the spindle is made by a cast spindle design, or by either turning and milling, based at least partly on the fact that the spindle is configured without difficult interior cuts.

16. Apparatus according to claim 1, wherein the apparatus comprises, or forms part of, a valve, including a diaphragm valve.

17. A diaphragm valve comprising:
a spindle having extending spindle portions configured with spindle glands;
a compressor having extending compressor portions configured with compressor glands, and
a snap ring configured to engage the spindle glands and the compressor glands in order to attach the spindle and the compressor together, so that the compressor may be quickly released from the spindle by releasing an engagement between the snap ring, the spindle glands and the compressor glands;
wherein the snap ring comprises one side having a flat circumferential surface configured to engage the spindle glands; and the snap ring comprises an opposite side having flat circumferential surface configured to engage the compressor glands;
the extending spindle portions comprise inwardly extending flanges configured to receive and engage outwardly extending flanges of a tube nut that forms part of a diaphragm attachment, and
the snap ring is configured to engage the extending spindle portions in order to resist outward movement of the inwardly extending flanges and maintain a coupling with the tube nut.

18. A diaphragm valve according to claim 17, wherein the coupling between the inwardly extending flanges of the extending spindle portions and the outwardly extending flanges of the tube nut primarily holds the compressor in place during operation.

* * * * *